United States Patent
Russell et al.

(10) Patent No.: US 9,217,705 B1
(45) Date of Patent: Dec. 22, 2015

(54) METHODS FOR ASSAYING IONIC MATERIALS USING AN INTEGRATED COMPUTATIONAL ELEMENT

(71) Applicant: Halliburton Energy Services, Inc., Houston, TX (US)

(72) Inventors: Aaron Gene Russell, Humble, TX (US); Johanna Haggstrom, Kingwood, TX (US); Robert P. Freese, Pittsboro, NC (US)

(73) Assignee: Halliburton Energy Services, Inc., Houston, TX (US)

( * ) Notice: Subject to any disclaimer, the term of this patent is extended or adjusted under 35 U.S.C. 154(b) by 55 days.

(21) Appl. No.: 14/362,434

(22) PCT Filed: Sep. 30, 2013

(86) PCT No.: PCT/US2013/062602
§ 371 (c)(1),
(2) Date: Jun. 3, 2014

(87) PCT Pub. No.: WO2015/047388
PCT Pub. Date: Apr. 2, 2015

(51) Int. Cl.
*G01J 3/46* (2006.01)
*G01N 21/27* (2006.01)
*G01N 33/44* (2006.01)

(52) U.S. Cl.
CPC .............. *G01N 21/27* (2013.01); *G01N 33/442* (2013.01); *G01N 2201/061* (2013.01)

(58) Field of Classification Search
CPC ................. G01J 3/02; G01J 3/50; G01J 3/51; G01J 3/52; G01J 3/524; G01J 3/46; G01N 21/27; G01N 33/44

USPC .................................................. 356/402–425
See application file for complete search history.

(56) References Cited

U.S. PATENT DOCUMENTS

| | | | |
|---|---|---|---|
| 5,039,491 A | 8/1991 | Saaski et al. |
| 6,198,531 B1 | 3/2001 | Myrick et al. |
| 6,529,276 B1 | 3/2003 | Myrick |
| 7,123,844 B2 | 10/2006 | Myrick |
| 7,834,999 B2 | 11/2010 | Myrick et al. |
| 7,911,605 B2 | 3/2011 | Myrick et al. |
| 7,920,258 B2 | 4/2011 | Myrick et al. |
| 8,204,565 B2 | 6/2012 | Arnold et al. |

(Continued)

FOREIGN PATENT DOCUMENTS

| WO | 2005041746 A2 | 5/2005 |
|---|---|---|
| WO | 2015047388 A1 | 4/2015 |

OTHER PUBLICATIONS

International Search Report and Written Opinion for PCT/US2013/62602 dated May 9, 2014.

*Primary Examiner* — Abdullahi Nur
(74) *Attorney, Agent, or Firm* — McDermott Will & Emery LLP; Craig W. Roddy

(57) ABSTRACT

The binding state of ionic materials, including metal ions, in a fluid phase can be determined using an integrated computational element. Methods for determining the binding state of an ionic material in a fluid phase can comprise optically interacting electromagnetic radiation with an ionic material and one or more integrated computational elements, the ionic material being located in a fluid phase while being optically interacted with the electromagnetic radiation; and determining one or more binding states of the ionic material in the fluid phase, using the one or more integrated computational elements.

25 Claims, 3 Drawing Sheets

(56) References Cited

U.S. PATENT DOCUMENTS

| | | |
|---|---|---|
| 8,349,453 B2 | 1/2013 | Char et al. |
| 8,619,256 B1 | 12/2013 | Pelletier et al. |
| 2007/0177240 A1* | 8/2007 | Van Beek ........... A61B 5/14532 359/196.1 |
| 2009/0073433 A1 | 3/2009 | Myrick et al. |
| 2009/0182693 A1 | 7/2009 | Fulton et al. |
| 2009/0219538 A1 | 9/2009 | Myrick et al. |
| 2009/0219539 A1 | 9/2009 | Myrick et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032334 A1 | 2/2013 | Freese et al. |
| 2013/0032340 A1 | 2/2013 | Freese et al. |
| 2013/0032344 A1 | 2/2013 | Freese et al. |
| 2013/0032345 A1 | 2/2013 | Freese et al. |
| 2013/0032545 A1 | 2/2013 | Freese et al. |

* cited by examiner

METHODS FOR ASSAYING IONIC MATERIALS USING AN INTEGRATED COMPUTATIONAL ELEMENT

BACKGROUND

The present disclosure generally relates to methods for assaying ionic materials, and, more specifically, to methods for assaying ionic materials using an integrated computational element to determine their binding state.

The analysis of ionic materials, both inorganic and organic in nature, is ubiquitous throughout numerous industrial processes. In many such cases, it can be desirable to determine the total quantity and/or types of ionic materials that are present in a fluid phase. Although some ionic materials can be readily assayed by routine spectroscopic techniques to determine their overall concentration of a fluid phase, certain types of ionic materials are much less readily analyzed by spectroscopy. For ionic materials that are not readily analyzable by routine spectroscopic techniques, their overall concentration in a fluid phase can sometimes be determined by various wet analytical techniques such as, for example, colligative property measurements and ion chromatography. For both spectroscopic and wet analytical techniques, interfering substances can be problematic for the analyses, and substantial sample preparation can sometimes be involved.

Although the total concentration of an ionic material in a fluid phase can represent a useful process diagnostic, an ionic material's total concentration may inaccurately represent the true nature of the ionic material in the fluid phase. For example, an ionic material can often be present in a fluid phase in various "complexed" or "bound" states, or it can simply be solvated by the fluid phase, the latter representing "free" or "unbound" ionic material. These groups of terms will be used synonymously herein. "Complexed" and "free" ionic materials can often behave very differently in a fluid phase, and as a result, the total ionic concentration may not be a representative diagnostic by which to judge or regulate an ongoing process. For example, a "complexed" Ionic material may be non-reactive and/or non-damaging in a process, but a "free" ionic material may be highly problematic. As a specific example, "free" metal ions may be particularly prone to scale formation in some instances. Collectively, various "complexed" and "free" ionic materials will be referred to herein as the "ionic species" or "binding states" of an ionic material.

Although certain ionic materials can be readily analyzed by spectroscopy to determine their overall concentration in a fluid phase, it can sometimes be much more difficult to determine the various fluid phase binding states of the ionic material, particularly by spectroscopy. If different regions of a spectrum can be conclusively identified as being produced predominantly by a particular binding state of an ionic material, an estimated binding state distribution can be obtained. However, the spectral differences between ionic materials in various binding states are often not well distinguished from one another by conventional spectroscopy, and the ability to successfully deconvolute a spectrum to determine the presence of various binding states can often be a matter of chance. Even when spectral deconvolution is possible in principle, the analyses can be costly, time-consuming, and extremely sensitive to the presence of interfering substances. Moreover, conventional spectroscopic instruments often require precise calibration and controlled operating conditions that can sometimes be unsuitable for field or process environments.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

Figure 1:
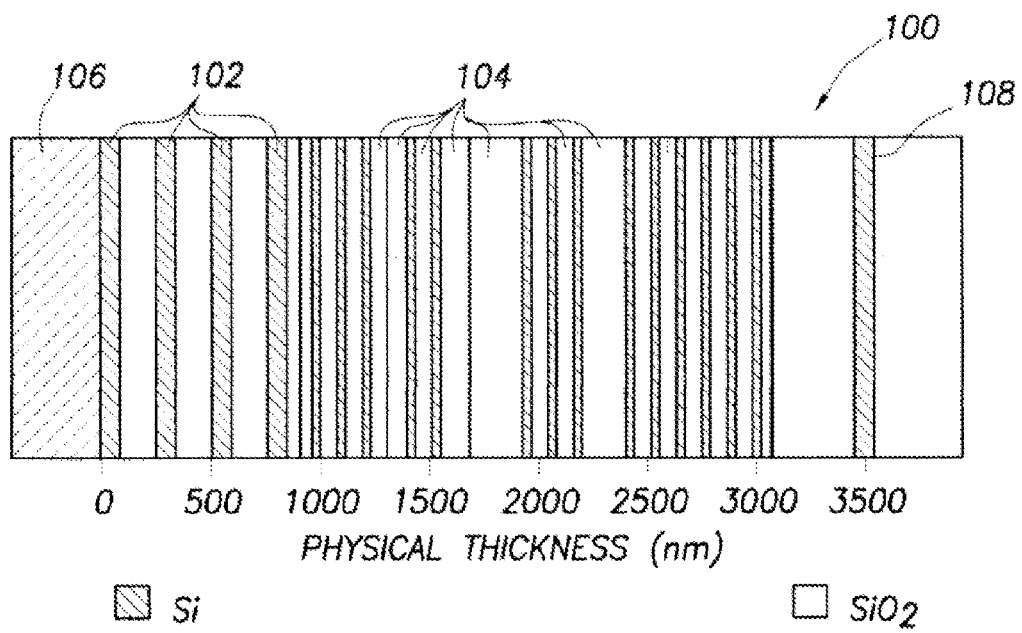
FIG. 1 shows a schematic of an illustrative integrated computational element (ICE).

The present disclosure generally relates to methods for assaying ionic materials, and, more specifically, to methods for assaying ionic materials using an integrated computational element to determine their binding state.

As described above, there may be several difficulties associated with conventional analyses of ionic materials, particularly for determining the distribution and relative abundance of their various binding states in a fluid phase. In many instances, such analyses may be specialized for particular ionic materials and not broadly applicable, especially in the presence of interferents, or the analyses may not proceed rapidly enough to satisfy various process requirements. These difficulties can be especially pronounced for metal ions. Moreover, for analyses conducted in field or process environments, including those of the oilfield services industry, conventional spectroscopic instruments may be difficult to deploy and maintain due to their sensitive hardware and typical need for controlled analysis conditions.

In contrast to conventional spectroscopic analyses, which may be sensitive to the presence of interferents and require time-consuming sample processing and/or spectral deconvolution techniques, the methods described herein may be performed much more rapidly to assay for various binding states of an ionic material in a fluid phase without significant influence from potential interferents. More specifically, the methods described herein utilize optical computing devices containing one or more integrated computational elements (ICE) in conjunction with analyzing for the presence of one or binding states of an ionic material in a fluid phase. Further disclosure regarding integrated computational elements and their advantages in this regard is presented below. Each integrated computational element within an optical computing device can be specifically configured to analyze for a particular binding state of an ionic material, even in the presence of interferents, based on the spectral perturbation that the ionic material produces in each state. Specifically, unbound ionic materials perturb the spectrum of a fluid phase differently than do bound ionic materials, and various bound states of an ionic material also differentially perturb a fluid phase spectrum. Thus, by using an integrated computational element configured for assaying a particular binding state of an ionic material, the abundance of the binding state can be quantified. Armed with detailed information regarding the abundance and distribution of various binding states of an ionic material in a fluid phase, an operator can then make more informed process control decisions, as further discussed herein.

Using one or more integrated computational elements for determining a binding state of an ionic material may present a number of advantages. A leading advantage is that measurements made using an integrated computational element are much less influenced by the presence of interferents than are other types of analyses, including conventional spectroscopic analyses, thereby allowing an ionic material to be assayed under a much broader array of conditions than is otherwise typically possible. Integrated computational elements and their associated hardware are also much more robust and less sensitive to corruption by field or process environments than are conventional spectroscopic instruments. Moreover, integrated computational elements and their associated hardware can produce extremely rapid analytical output, thereby making them suitable for determining one or more binding states of an ionic material in real-time or near real-time. All of these features can prove advantageous when analyzing for a binding state of an ionic material in a process or like environment.

In addition to the foregoing, the methods described herein may allow mechanistic insights to be gained that are difficult or impossible to determine by other analysis techniques, spectroscopic or otherwise. For example, the crosslinking and breaking mechanism of metal-crosslinked polymers may be followed by determining a progression of metal-binding states over time. These types of analyses are not readily performed by conventional spectroscopic techniques, whereas they may be performed readily, in real-time or near real-time, using an integrated computational element. In addition, such analyses using an integrated computational element may provide mechanistic insight into the potential re-healing of a broken polymer fluid, which is not believed to be possible by any conventional analytical techniques. Analyses using an integrated computational element to monitor polymer crosslinking may be of particular relevance in certain treatment operations conducted in the oilfield services industry, as discussed further hereinafter.

From an operational standpoint, the methods described herein may be particularly advantageous, since they may allow early intervention to take place in a process in which an ionic material can be present in one or more binding states. For example, a treatment operation conducted using a fluid phase containing an ionic material may be monitored to determine if the treatment operation has been successful, as determined by the binding state of the ionic material following the treatment operation. If a desired binding state of the ionic material has not been attained, various process intervention operations may take place. More specific examples in this regard follow hereinbelow. By determining the binding state (s) of an ionic material during a treatment operation and intervening as needed, significant cost and time savings may be realized. For example, by knowing the binding states of an ionic material and possibly intervening in a treatment operation, one may avoid having to repeat the treatment operation and/or possibly remediating subterranean formation damage.

One or more illustrative embodiments incorporating the disclosure herein are presented below. Not all features of an actual implementation are described or shown in this application for the sake of clarity. It is to be understood that in the development of an actual embodiment incorporating the present disclosure, numerous implementation-specific decisions must be made to achieve the developer's goals, such as compliance with system-related, business-related, government-related and other constraints, which may vary by implementation and from time to time. While a developer's efforts might be complex and time-consuming, such efforts would be, nevertheless, a routine undertaking for one having ordinary skill in the art and the benefit of this disclosure.

The theory behind optical computing and a description of some conventional optical computing devices are provided in more detail in the following commonly owned United States patents and United States patent application Publications, each of which is incorporated herein by reference in its entirety: U.S. Pat. Nos. 6,198,531; 6,529,276; 7,123,844; 7,834,999; 7,911,605; 7,920,258; 2009/0219538; 2009/0219539; and 2009/0073433. Accordingly, the theory behind optical computing will not be discussed in any extensive detail herein unless needed to better describe one or more embodiments of the present disclosure. Unlike conventional spectroscopic instruments, which produce a spectrum needing further interpretation to obtain a result, the ultimate output of optical computing devices is a real number that can be correlated in some manner with a binding state of a particular ionic material. For example, in the embodiments described herein, the optical computing device may output a real number that may be correlated with a concentration of a first binding state of an ionic material. A second integrated computational element and associated detection hardware in the optical computing device may be used to determine the concentration of a second binding state of the ionic material. The first and second binding states may exist at different times in a fluid phase, or they may be present together in a fluid phase at the same time. The operational simplicity of optical computing devices allows them to rapidly produce an output, in real-time or near real-time, in some embodiments. Correlation of the numerical output for a given binding state of an ionic material may take place by comparing the numerical output obtained from a fluid phase having an unknown concentration of an ionic material in a particular binding state with the numerical output obtained from a previously measured fluid phase having a known concentration of the ionic material in the given binding state.

Figure 4:
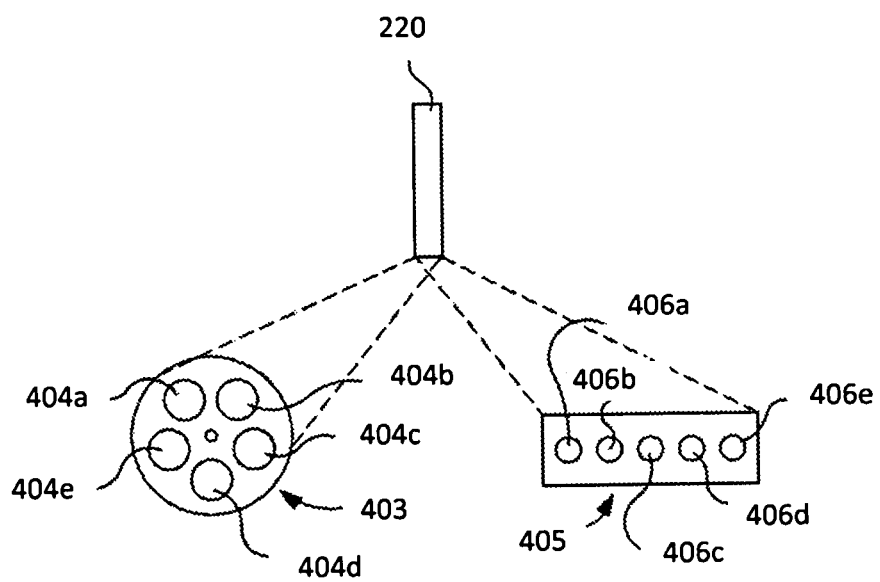
FIG. 4 shows a schematic of illustrative arrays of integrated computational elements.

In addition, significant benefits can sometimes be realized by combining the outputs from two or more integrated computational elements with one another, even when analyzing for a single binding state of interest. Specifically, in some instances, significantly increased detection accuracy may be realized. Techniques for combining the output of two or more integrated computational elements with one another, particularly computationally combining the outputs, are described in commonly owned U.S. patent application Ser. Nos. 13/456,255; 13/456,264; 13/456,283; 13/456,302; 13/456,327; 13/456,350; 13/456,379; 13/456,405; and 13/456,443, each filed on Apr. 26, 2012 and incorporated herein by reference in its entirety. Any of the methods described herein may be carried out by combining the outputs of two or more integrated computational elements with one another. The integrated computational elements whose outputs are being combined may be associated or disassociated with the binding state of interest, display a positive or negative response when analyzing the binding state, or any combination thereof. Illustrative configurations of optical computing devices containing two or more integrated computational elements are shown in FIG. 4 and described in more detail hereinbelow.

As alluded to above, the operational simplicity of optical computing devices makes them rugged and well suited for field or process environments, including deployment within a subterranean formation. Uses of conventional optical computing devices for analyzing fluids commonly encountered in the oil and gas industry, including while deployed within a subterranean formation, are described in commonly owned United States Patent Application Publications 2013/0031970, 2013/0031971, 2013/0031972, 2013/0032333, 2013/0032334, 2013/0032340, 2013/0032344, 2013/0032345 and 2013/0032545, each of which is incorporated herein by reference in its entirety.

As used herein, the term "ionic material" refers to a substance that bears a non-zero charge when in an unbound state or in a bound state.

As used herein, the term "bound state" refers to a condition that exists when an ionic material is ligated with a complexing species. As used herein, the term "unbound state" refers to a condition that exists when an ionic material is substantially only solvated by solvent molecules in a fluid phase. In either state, the overall charge may be balanced by a counterion of opposite charge.

As used herein, the term "electromagnetic radiation" refers to radio waves, microwave radiation, infrared and near-infrared radiation, visible light, ultraviolet radiation, X-ray radiation, and gamma ray radiation.

As used herein, the term "optically interact" and variants thereof refer to the reflection, transmission, scattering, diffraction, or absorption of electromagnetic radiation through or from a fluid phase or one or more integrated computational elements. Accordingly, optically interacted electromagnetic radiation refers to electromagnetic radiation that has been reflected, transmitted, scattered, diffracted, absorbed, emitted, or radiated from a fluid phase or an integrated computational element.

As used herein, the term "optical computing device" refers to an optical device that is configured to receive an input of electromagnetic radiation associated with an ionic material and produce an output of electromagnetic radiation from a processing element arranged within the optical computing device. The electromagnetic radiation may optically interact with the ionic material in a fluid phase before or after optically interacting with the optical computing device. The processing element may be, for example, an integrated computational element (ICE), also known as a multivariate optical element (MOE) or an ICE CORE (Halliburton Energy Services), an illustrative example of which is described in more detail below. The electromagnetic radiation that optically interacts with the processing element may be changed so as to be readable by a detector, such that an output of the detector can be correlated to one or more binding states of the ionic material. The output of electromagnetic radiation from the processing element can comprise reflected, transmitted, and/or dispersed electromagnetic radiation. Whether the detector analyzes reflected, transmitted, or dispersed electromagnetic radiation may be dictated by the structural parameters of the optical computing device as well as other considerations known to one having ordinary skill in the art. In addition, emission and/or scattering of the electromagnetic radiation, for example, via fluorescence, luminescence, Raman, Mie, and/or Raleigh scattering, can also be monitored by the optical computing devices.

As used herein, the term "formation" or "subterranean formation" refers to a body or section of geologic strata, structure, formation or other subsurface solid or collected material that is sufficiently distinctive and continuous with respect to other geologic strata or characteristics that it can be mapped, for example, by seismic techniques. A formation can be a body of geologic strata of predominantly one type or a combination of types, or a fraction of strata having substantially common set of characteristics. A formation can contain one or more hydrocarbon-bearing zones. The terms "formation," "hydrocarbon-bearing subterranean formation," "reservoir," and "interval" may be used interchangeably herein, but may generally be used to denote progressively smaller subsurface regions, zones, or volumes. More specifically, a geologic formation may generally be the largest subsurface region, a subterranean formation may generally be a region within the geologic formation and may generally be a hydrocarbon-bearing zone (a formation, reservoir, or interval having oil, gas, heavy oil, and any combination thereof), and an interval may generally refer to a sub-region or portion of a reservoir. A hydrocarbon-bearing zone can be separated from other hydrocarbon-bearing zones by zones of lower permeability such as mudstones, shales, or shale-like (highly compacted) sands. In one or more embodiments, a hydrocarbon-bearing zone may include heavy oil in addition to sand, clay, or other porous solids.

As used herein, the term "fluid" refers to any substance that is capable of flowing, including particulate solids, liquids, gases, slurries, emulsions, powders, muds, glasses, any combination thereof, and the like. In some embodiments, the fluid can comprise an aqueous fluid, including water, mixtures of water and water-miscible fluids, brine, and the like. In some embodiments, the fluid can comprise a non-aqueous fluid, including organic compounds (i.e., hydrocarbons, oil, a refined component of oil, petrochemical products, and the like). In some embodiments, the fluid can comprise a treatment fluid or a formation fluid.

As used herein, the term "formation fluid" refers to a fluid phase that natively occurs within a subterranean formation. Illustrative fluid phases that are found in a subterranean formation and which may be analyzed by the methods described herein to determine one or more binding states of an ionic material therein include, for example, oil, liquid hydrocarbons, gaseous hydrocarbons, natural gas, reservoir brines, formation water, any combination thereof, and the like.

As used herein, the term "treatment fluid" refers to a fluid that is placed in a location (e.g., a subterranean formation or a pipeline) in order to perform a desired function. Treatment fluids can be used in a variety of subterranean operations, including, but not limited to, drilling operations, production treatments, stimulation treatments, remedial treatments, fluid diversion operations, fracturing operations, secondary or tertiary enhanced oil recovery (EOR) operations, and the like. As used herein, the terms "treat," "treatment," "treating," and other grammatical equivalents thereof refer to any operation that uses a fluid in conjunction with performing a desired function and/or achieving a desired purpose. The terms "treat," "treatment," and "treating," as used herein, do not imply any particular action by the fluid or any particular component thereof unless otherwise specified. Treatment fluids for subterranean operations can include, for example, drilling fluids, fracturing fluids, acidizing fluids, conformance treatment fluids, damage control fluids, remediation fluids, scale removal and inhibition fluids, diversion fluids, chemical floods, and the like. Any of these types of treatment fluids may contain an ionic material, which may be present in one or more binding states therein.

As used herein, the term "produced fluid" refers to a fluid phase obtained (i.e., produced) from a subterranean formation following a treatment operation.

As used herein, the terms "real-time" and "near real-time" refer to an output from an integrated computational element that is produced on substantially the same time scale as the optical interrogation of a substance with electromagnetic radiation. That is, a "real-time" or "near real-time" output does not take place offline after data acquisition and post-processing techniques. An output that is returned in "real-time" may be returned essentially instantaneously. A "near real-time" output may be returned after a brief delay, which may be associated with processing or data transmission time, or the like. It will be appreciated by one having ordinary skill in the art that the rate at which an output is received may be dependent upon the processing and data transmission rate.

FIG. 1 shows a schematic of an illustrative integrated computational element (ICE) 100. As illustrated in FIG. 1, ICE 100 may include a plurality of alternating layers 102 and 104 of varying thicknesses disposed on optical substrate 106. In general, the materials forming layers 102 and 104 have indices of refraction that differ (i.e., one has a low index of refraction and the other has a high index of refraction), such as Si and $SiO_2$. Other suitable materials for layers 102 and 104 may include, but are not limited to, niobia and niobium, germanium and germania, MgF, and SiO. Additional pairs of materials having high and low indices of refraction can be envisioned by one having ordinary skill in the art, and the composition of layers 102 and 104 is not considered to be particularly limited. In some embodiments, the material within layers 102 and 104 can be doped, or two or more materials can be combined in a manner to achieve a desired optical response. In addition to solids, ICE 100 may also contain liquids (e.g., water) and/or gases, optionally in combination with solids, in order to produce a desired optical response. The material forming optical substrate 106 is not considered to be particularly limited and may comprise, for example, BK-7 optical glass, quartz, sapphire, silicon, germanium, zinc selenide, zinc sulfide, various polymers (e.g., polycarbonates, polymethylmethacrylate, polyvinylchloride, and the like), diamond, ceramics, and the like. Opposite to optical substrate 106, ICE 100 may include layer 108 that is generally exposed to the environment of the device or installation in which it is used.

The number, thickness, and spacing of layers 102 and 104 may be determined using a variety of approximation methods based upon a conventional spectroscopic measurement of a sample. These methods may include, for example, inverse Fourier transform (IFT) of the optical transmission spectrum and structuring ICE 100 as a physical representation of the IFT. The approximation methods convert the IFT into a structure based on known materials with constant refractive indices.

It should be understood that illustrative ICE 100 of FIG. 1 has been presented for purposes of illustration only. Thus, it is not implied that ICE 100 is predictive for any particular binding state of a given ionic material. Furthermore, it is to be understood that layers 102 and 104 are not necessarily drawn to scale and should therefore not be considered as limiting of the present disclosure. Moreover, one having ordinary skill in the art will readily recognize that the materials comprising layers 102 and 104 may vary depending on factors such as, for example, the types of substances being analyzed and the ability to accurately conduct their analysis, cost of goods, and/or chemical compatibility issues.

The weightings that the layers 102 and 104 of ICE 100 apply at each wavelength are set to the regression weightings described with respect to a known equation, or data, or spectral signature. Briefly, ICE 100 may be configured to perform the dot product of the input electromagnetic radiation into ICE 100 and produce a desired loaded regression vector represented by each layer 102 and 104 for each wavelength. As a result, the output electromagnetic radiation intensity of the ICE 100 may be correlated to a particular binding state of a given ionic Material. Further details regarding how ICE 100 is able to distinguish and process electromagnetic radiation are described in U.S. Pat. Nos. 6,198,531, 6,529,276, and 7,920,258, each of which was previously incorporated by reference in its entirety.

It is to be recognized that the embodiments herein may be practiced with various blocks, modules, elements, components, methods and algorithms, which can be implemented through using computer hardware, software and combinations thereof. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the spirit and scope of the embodiments expressly described.

Computer hardware used to implement the various illustrative blocks, modules, elements, components, methods and algorithms described herein can include a processor configured to execute one or more sequences of instructions, programming or code stored on a readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable PROM), registers, hard disks, removable disks, CD-ROMS, DVDs, or any other like suitable storage device.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and software.

As used herein, a machine-readable medium will refer to any non-transitory medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Figure 2:
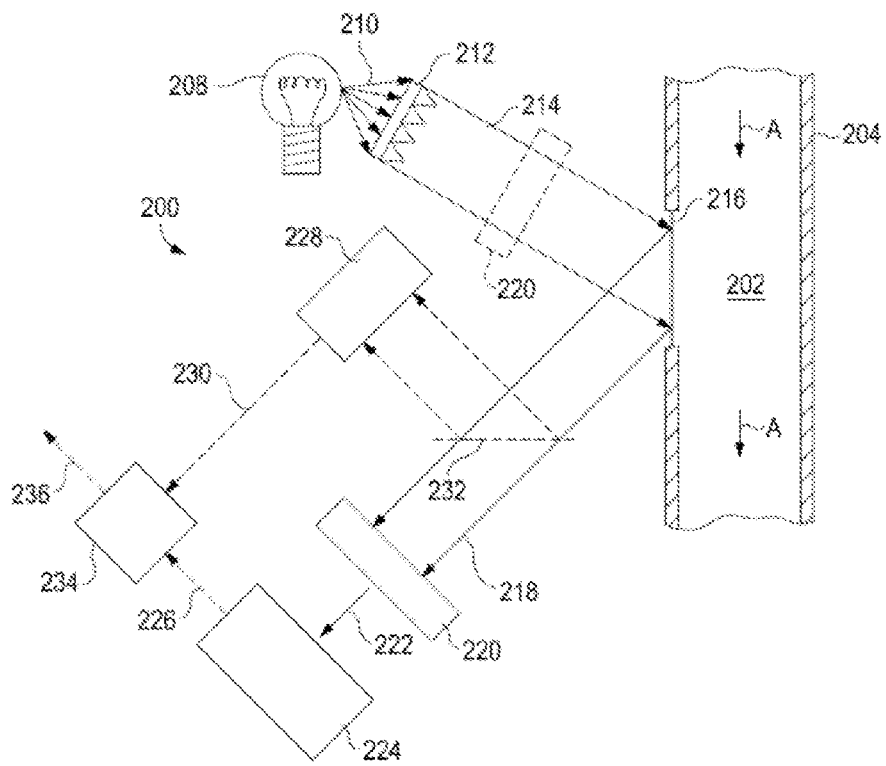
FIGS. 2 and 3 show schematics of illustrative optical computing devices employing an integrated computational element.
Figure 3:
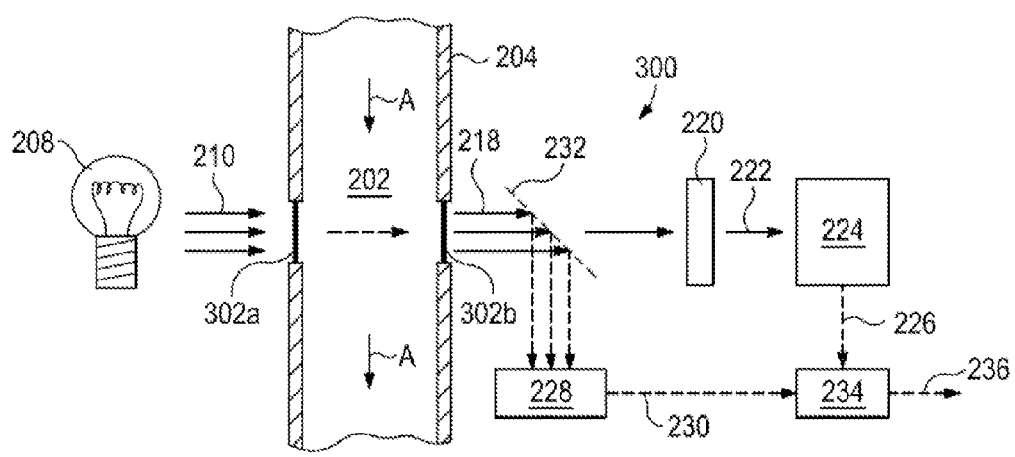

Illustrative configurations for optical computing devices containing a single integrated computational element will now be described in more detail. It is to be recognized that the device configurations depicted in FIGS. 2 and 3 are illustrative in nature only and can be modified extensively to accommodate the requirements of a particular analysis. As non-limiting examples, the single integrated computation elements of FIGS. 2 and 3 may be replaced by multiple integrated computational elements, the outputs of which may or may not be computationally combined with one another. In some embodiments, multiple integrated computational elements may be placed in series or parallel, or disposed in an array on a movable assembly such that the electromagnetic radiation optically interacts with different integrated computational elements over time, as depicted in FIG. 4. The different integrated computational elements may be used to analyze for distinct binding states of an ionic material, or the output from one or more integrated computational elements may be computationally combined to determine a single binding state.

FIG. 2 shows an illustrative optical computing device 200 configured for monitoring fluid 202 by reflection, according to one or more embodiments. In the illustrated embodiment, fluid 202 may be contained or otherwise flowing within flow path 204. Flow path 204 may be a flow line, a pipeline, a wellbore, an annulus defined within a wellbore, or any flow lines or pipelines extending to/from a wellbore. Fluid 202 within flow path 204 may be flowing in the general direction indicated by the arrows A (i.e., from upstream to downstream). Portions of flow path 204 may be arranged substantially vertically, substantially horizontally, or any directional configuration therebetween, without departing from the scope of the disclosure.

Optical computing device 200 may be configured to determine a binding state of an ionic material within fluid 202, such as whether the ionic material is unbound or bound to various substances therein. Device 200 may include electromagnetic radiation source 208 configured to emit or otherwise generate electromagnetic radiation 210. Electromagnetic radiation source 208 may be any device capable of emitting or generating electromagnetic radiation, as defined herein. For example, electromagnetic radiation source 208 may be a light bulb, a light emitting diode (LED), a laser, a blackbody, a photonic crystal, an X-Ray source, any combination thereof, and the like. In some embodiments, lens 212 may be configured to collect or otherwise receive electromagnetic radiation 210 and direct beam 214 of electromagnetic radiation 210 toward fluid 202. Lens 212 may be any type of optical device configured to transmit or otherwise convey electromagnetic radiation 210 as desired, such as a normal lens, a Fresnel lens, a diffractive optical element, a holographic graphical element, a mirror (e.g., a focusing mirror), or a type of collimator. In some embodiments, lens 212 may be omitted from device 200 and electromagnetic radiation 210 may instead be directed toward fluid 202 directly from electromagnetic radiation source 208.

In some embodiments, device 200 may also include sampling window 216 arranged adjacent to or otherwise in contact with fluid 202 for detection purposes. Sampling window 216 may be made from a variety of transparent, rigid or semi-rigid materials that are configured to allow transmission of electromagnetic radiation 210 therethrough. For example, sampling window 216 may be made of glasses, plastics, semiconductors, crystalline materials, polycrystalline materials, hot or cold-pressed powders, any combination thereof, and the like. After passing through sampling window 216, electromagnetic radiation 210 impinges upon and optically interacts with fluid 202. As a result, optically interacted electromagnetic radiation 218 is generated by and reflected from fluid 202. It is to be recognized, however, that alternative configurations of device 200 may allow optically interacted electromagnetic radiation 218 to be generated by being transmitted, scattered, diffracted, absorbed, emitted, or re-radiated by and/or from fluid 202, without departing from the scope of this disclosure.

Optically interacted electromagnetic radiation 218 generated by the interaction with fluid 202 may be directed to or otherwise be received by ICE 220 arranged within the device 200. ICE 220 may be a spectral component substantially similar to ICE 100 described above with reference to FIG. 1. Accordingly, ICE 220 may be configured to receive the optically interacted electromagnetic radiation 218 and produce modified electromagnetic radiation 222 corresponding to a binding state of an ionic material within fluid 202. In particular, modified electromagnetic radiation 222 is electromagnetic radiation that has optically interacted with ICE 220, whereby an approximation of the regression vector corresponding to the binding state of the ionic material is obtained.

While FIG. 2 depicts ICE 220 as receiving reflected electromagnetic radiation from fluid 202, ICE 220 may be arranged at any point along the optical train of device 200, without departing from the scope of this disclosure. For example, in one or more embodiments, ICE 220 (as shown in dashed) may be arranged within the optical train prior to the sampling window 216, while obtaining substantially the same results. In other embodiments, ICE 220 may generate modified electromagnetic radiation 222 through reflection, instead of transmission therethrough.

Modified electromagnetic radiation 222 generated by ICE 220 may subsequently be conveyed to detector 224 for quantification of the signal. Detector 224 may be any device capable of detecting electromagnetic radiation, and may be generally characterized as an optical transducer. In some embodiments, detector 224 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), a photodiode, any combination thereof, and the like. Other detectors known to one having ordinary skill in the art may also be used.

In some embodiments, detector 224 may be configured to produce output signal 226 in real-time or near real-time in the form of a voltage (or current) that corresponds to a binding state of an ionic material in fluid 202. The voltage returned by detector 224 is essentially the dot product of the optical interaction of optically interacted electromagnetic radiation 218 with ICE 220 as a function of the magnitude of the quantity of a particular binding state that is present. As such, output signal 226 produced by detector 224 and the abundance of the binding state may be related, such as directly proportional, for example. In other embodiments, however, the relationship may correspond to a polynomial function, an exponential function, a logarithmic function, and/or a combination thereof.

In some embodiments, device 200 may include second detector 228, which may be similar to first detector 224 in that it may be any device capable of detecting electromagnetic radiation. Second detector 228 may be used to detect radiating deviations stemming from electromagnetic radiation source 208. Undesirable radiating deviations can occur in the intensity of electromagnetic radiation 210 due to a wide variety of reasons and potentially cause various negative effects on device 200. These negative effects can be particularly detrimental for measurements taken over a period of time. In some embodiments, radiating deviations can occur as a result of a build-up of film or material on sampling window 216, which may have the effect of reducing the amount and quality of electromagnetic radiation ultimately reaching first detector 224. Without proper compensation, such radiating deviations may result in false readings that result in output signal 226 no longer being correlatable with the binding state of interest.

To compensate for radiating deviations, second detector 228 may be configured to generate compensating signal 230 that is generally indicative of the radiating deviations of electromagnetic radiation source 208, thereby normalizing output signal 226 generated by first detector 224. As illustrated, second detector 228 may be configured to receive a portion of optically interacted electromagnetic radiation 218 via beamsplitter 232 in order to detect the radiating deviations. In other embodiments, however, second detector 228 may be arranged to receive electromagnetic radiation from any portion of the optical train in device 200 in order to detect the radiating deviations, without departing from the scope of this disclosure.

In some embodiments, output signal 226 and compensating signal 230 may be conveyed to or otherwise received by signal processor 234 that is communicably coupled to both of detectors 224 and 228. Signal processor 234 may be a computer including a processor and a machine-readable storage medium having instructions stored thereon, which, when executed by signal processor 234, result in optical computing device 200 performing a number of operations, such as determining a binding state of an ionic material in fluid 202. Signal processor 234 may utilize an artificial neural network, such as those described in commonly owned United States Patent Application Publication 2009/0182693, which is incorporated herein by reference in its entirety. Signal processor 234 may also be configured to computationally combine the outputs of two or more integrated computational elements, if desired, for quantifying a particular binding state of interest.

In real-time or near real-time, signal processor 234 may be configured to provide output signal 236 corresponding to a binding state of interest for an ionic material in fluid 202. Output signal 236 may be readable by an operator who can consider the results and take appropriate action, if needed. In some embodiments, output signal 236 may be conveyed, either wired or wirelessly, to an operator for consideration. In other embodiments, output signal 236 may be recognized by signal processor 234 as being within or outside a predetermined or preprogrammed range of suitable values for operation and may alert an operator in the event of an out-of-range value. In still other embodiments, signal processor 234 may autonomously undertake an appropriate corrective action in order to return output signal 236 to within a desired range.

FIG. 3 shows an illustrative optical computing device 300 configured for monitoring a fluid 202 by transmission, according to one or more embodiments. Optical computing device 300 may be similar in some respects to optical computing device 200 of FIG. 2, and therefore may be best understood with reference thereto, where like reference characters have been used to enumerate elements having similar functions. Unlike device 200, however, optical computing device 300 of FIG. 3 may be configured to transmit electromagnetic radiation 210 through fluid 202 via first sampling window 302a and second sampling window 302b arranged radially-opposite first sampling window 302a on flow path 204. First and second sampling windows 302a and 302b may be similar to sampling window 216 described above in FIG. 2 and therefore will not be described in detail again.

As electromagnetic radiation 210 passes through fluid 202 via first and second sampling windows 302a and 302b, it optically interacts with fluid 202, and optically interacted electromagnetic radiation 218 is subsequently directed to or is otherwise received by ICE 220. It is again noted that, ICE 220 may be arranged at any point along the optical train of the device 300, without departing from the scope of this disclosure. For example, in one or more embodiments, ICE 220 may be arranged within the optical train prior to first sampling window 302a. In yet other embodiments, ICE 220 may generate modified electromagnetic radiation 222 through reflection, instead of transmission therethrough.

Modified electromagnetic radiation 222 generated by ICE 220 is subsequently conveyed to detector 224 for quantification of the signal and generation of output signal 226, which corresponds to a binding state of an ionic material in fluid 202. Device 300 may also include second detector 228 for detecting radiating deviations stemming from electromagnetic radiation source 208. As illustrated, second detector 228 may be configured to receive a portion of the optically interacted electromagnetic radiation 218 via beamsplitter 232 in order to detect radiating deviations and produce compensating signal 230. Output signal 226 and compensating signal 230 may then be conveyed to or otherwise received by signal processor 234 to provide, in real-time or near real-time, output signal 236 that corresponds to a binding state of an ionic material in fluid 202.

In some embodiments, the single ICE 220 of FIGS. 2 and 3 may be replaced by an array of integrated computational elements, as illustratively depicted in FIG. 4. By moving the integrated computational elements of the depicted arrays with respect to the electromagnetic radiation, different integrated computational elements may be exposed to the electromagnetic radiation over time. In some embodiments, the array may comprise rotating disc 403 containing integrated computational elements 404a-404e thereon. In other embodiments, the array may comprise movable assembly 405 having integrated computational elements 406a-406e thereon, in which movable assembly 405 is shifted or reciprocated laterally over the course of time to expose integrated computational elements 406a-406e to electromagnetic radiation. It is to be recognized that although the arrays of FIG. 4 have depicted five integrated computational elements in the array, any number may be present.

In some embodiments, methods described herein may comprise: optically interacting electromagnetic radiation with an ionic material and one or more integrated computational elements, the ionic material being located in a fluid phase while being optically interacted with the electromagnetic radiation; and determining one or more binding states of the ionic material in the fluid phase, using the one or more integrated computational elements. In some embodiments, the methods may further comprise detecting the electromagnetic radiation that has optically interacted with the ionic material and the one or more integrated computational elements; and generating an output signal based on the detected electromagnetic radiation, where the output signal is correlatable to one or more binding states of the ionic material in the fluid phase. In some embodiments, the output signal may provide a measure of the quantity of a particular binding state of the ionic material that is present in the fluid phase.

In some embodiments, the methods may further comprise providing the electromagnetic radiation that optically interacts with the ionic material and the one or more integrated computational elements. In some embodiments, the electromagnetic radiation may be provided from an external source such as a lamp, a laser, a light-emitting diode (LED), a blackbody, or the like. The type of electromagnetic radiation that is optically interacted with the ionic material and the one or more integrated computational elements is not believed to be particularly limited. Suitable electromagnetic radiation sources may include visible light, infrared radiation, near-infrared radiation, ultraviolet radiation, X-ray radiation, gamma ray radiation, radio wave radiation, microwave radiation, any combination thereof, and the like. Particular types of electromagnetic radiation that optically interact strongly with the ionic material or a bound variant thereof may dictate the chosen type and specific wavelengths of electromagnetic radiation employed in the methods described herein.

In some embodiments, the electromagnetic radiation detected after optically interacting with the ionic material and the one or more integrated computational elements may lie in the near-infrared region of the electromagnetic spectrum. In some embodiments, the detected electromagnetic radiation may lie within a wavelength range of about 1000 nm to about 5000 nm, or a range of about 1000 nm to about 4000 nm, or a range of about 1000 nm to about 3000 nm. Other detected wavelength ranges are possible and can include, for example, detection in the radio wave region, the microwave radiation region, the infrared radiation region, the visible light region, the ultraviolet radiation region, the X-ray radiation region, the gamma ray radiation region, or any combination thereof. The particular detection region chosen will depend, at least in part, upon the nature of the optical interaction of the electromagnetic radiation with the particular ionic material or bound variant thereof. Moreover, one of ordinary skill in the art will be able to choose a suitable detector for use in detecting a particular type of electromagnetic radiation.

The type of ionic material whose binding state can be quantified according to the methods described herein is not believed to be particularly limited. In this regard, the binding states of both organic and inorganic ionic materials can be detected and quantified with the methods described herein. In more particular embodiments, the ionic material may be inorganic and comprise a metal ion. As discussed above, determination of the binding states of metal ions in a fluid phase can sometimes be problematic. In still more particular embodiments, the ionic material may comprise a metal ion that can form crosslinks between molecules of a crosslinkable polymer. Suitable metals ions for forming crosslinks between polymer molecules can include, for example, chromium ions, zirconium ions, aluminum ions, titanium ions, antimony ions, magnesium ions, calcium ions, and any combination thereof. Knowing the binding state of these metal ions and other types of metal ions may allow one to determine if effective crosslinking or breaking of a crosslinked polymer has occurred.

The methods described herein may also be of relevance to determine the scaling potential of metal ions in a fluid phase. Generally, metal ions in an unbound state in a fluid phase have a considerably greater scaling potential than do metal ions in a bound state. Illustrative metal ions with a high scaling potential in their unbound state include, for example, calcium ions, magnesium ions, and any combination thereof, although any metal ion in an unbound state represents some potential for scale formation to occur. Unbound metal ions may also have a high propensity to interact undesirably with scale control agents that may be used in mitigating that formation of scale during various types of industrial processes. Hence, it can be very desirable to know the binding state of a metal ion in a fluid phase.

As alluded to above, various binding states of an ionic material to a substance in a fluid phase may be determined using the methods described herein. Specifically, the methods described herein may determine one or more binding states of an ionic material in a fluid phase as a distribution of the ionic material between an unbound (i.e., "free") state and one or more bound states. In various embodiments, the one or more bound states can include, for example, a bound state to a polymer, a bound state to a ligand, a bound state to a polymer fragment, a bound state to a monomer, and any combination thereof. As used herein, the term "monomer" will refer to a single repeating unit of a polymer, and the term "polymer fragment" will refer to an oligomer comprising two or more monomers that are bonded to each other. As further alluded to above, the various bound and unbound states of a metal ion may be of considerable relevance toward the crosslinking of a polymer and formation of a gelled fluid therefrom.

Polymers that may be present in a fluid phase and interact in a binding state with an ionic material are not believed to be particularly limited. However, in more specific embodiments, the polymer may comprise a crosslinkable polymer, particularly a polymer that is crosslinkable by entering into a binding state with a metal ion. Particularly suitable crosslinkable polymers may include those utilized in the course of treating a subterranean formation by forming a gelled treatment fluid. In this regard, illustrative crosslinkable polymers that may be present in the fluid phase include, for example, biopolymers, particularly a polysaccharide or a modified polysaccharide. Illustrative polysaccharides may include, for example, a cellulose or modified cellulose, a guar or modified guar, a xanthan, a welan, a diutan, a scleroglucan, a succinoglycan, a chitosan, a chitin, a dextran, a starch, a sugar, any crosslinkable derivative thereof, or any combination thereof. Illustrative celluloses and modified celluloses may include, for example, carboxymethylcellulose, carboxymethylhydroxyethylcellulose, carboxyethylcellulose, hydroxyethylcellulose, and the like. Illustrative guars and modified guars may include, for example, hydroxypropylguar, carboxymethylhydroxypropylguar, carboxymethylguar, hydroxyethylguar, carboxymethylhydroxyethylguar, and the like. Other crosslinkable polymers that may be present in a fluid phase in concert with an ionic material, either in combination with a biopolymer or in lieu of a biopolymer, can include, for example, a polyacrylamide, a polyacrylate, a partially hydrolyzed polyacrylamide, a polymethacylamide, a polymethacrylate, a partially hydrolyzed methacrylamide, a polyester, a poly(orthoester), a polyanhydride, a polycarbonate, a polyamide, a polyphosphazene, a polyvinyl alcohol, a 2-acrylamido-2-methyl propane sulfonate-containing polymer or copolymer, a poly(vinyl pyrollidone), a poly(diallyldimethylammonium chloride), a poly(ethylene glycol), a poly(ethylene oxide), a polylysine, a poly(vinylamine), a poly(ethyleneimine), a poly(lactic acid), a poly(glycolic acid), any crosslinkable derivative thereof, and the like.

After forming a metal-crosslinked polymer, which may result in formation of a gelled fluid, the gelled fluid may be broken in some embodiments. In some embodiments, gel breaking may occur natively due to a reactant or temperature condition that is already present where the gelled fluid is deployed. In other embodiments, a breaker may be added to facilitate the breaking process. Illustrative breakers will be familiar to one having ordinary skill in the art and are not believed to be particularly limited in practicing the embodiments described herein. Breaking may decrease the viscosity of the fluid phase, depolymerize the polymer molecules, and/ or remove crosslinks between the polymer molecules. In some embodiments, the methods described herein may be used to distinguish between these various breaking processes. For example, the methods may be used to determine if unbound metal ions are present, possibly being indicative of crosslink removal, or if the metal ions remain bound to a monomer or a larger polymer fragment, possibly being indicative of polymer molecule scission. Thus, the methods described herein may be applicable both in the lab and in the field to determine the various factors that may be associated with establishing the binding state of an ionic material, thereby potentially allowing manipulation of the binding state and better utilization of the ionic material to take place.

Many industrial processes, including those conducted in the upstream energy industry, utilize treatment fluids, particularly viscosified treatment fluids. In some embodiments, the fluid phase in which the ionic material is present may comprise a treatment fluid. In some embodiments, the methods described herein may further comprise introducing the treatment fluid into a subterranean formation. Such treatment fluids may include, but are not limited to, fracturing fluids, drilling fluids, completion fluids, diversion fluids, gravel packing fluids, acidizing fluids, conformance fluids, the like, and any combination thereof. Further disclosure regarding particular types of treatment operations and control thereof are described hereinbelow. Generally, viscosified treatment fluids that are used in a subterranean formation in the course of performing a treatment operation are aqueous-based fluids that comprise a crosslinkable polymer, such as those described above.

In many cases, treatment fluids can be utilized in a gelled state when performing a treatment operation. For example, in a fracturing operation, a treatment fluid can be gelled to increase its viscosity and improve its ability to carry a proppant or other particulate material. In other cases, a gelled treatment fluid can be used to at least temporarily divert or block the flow of fluids within at least a portion of a subterranean formation. In either case, it can be desirable to know if a polymer has remained crosslinked and the treatment fluid possesses the capabilities for performing as intended. The methods described herein make such analyses possible by allowing one to determine the binding states of an ionic material, such as a metal ion.

In some embodiments, the methods described herein may comprise determining if the fluid phase contains a crosslinked polymer by determining the one or more binding states of the ionic material. For example, if unbound metal ions or metal ions only bound to a polymer fragment are detected, one may infer that a crosslinked polymer is no longer present.

In further embodiments, the methods described herein may allow one to determine an oxidation state of a metal ion. Specifically, a metal ion in a first oxidation state may exhibit significantly different binding properties to a complexing species than does a metal ion in a second oxidation state. Thus, by determining the particular binding state of a metal ion that is present in a fluid phase, the oxidation state of the metal ion may be inferred. For example, a metal ion in a first oxidation state may have limited binding affinity for a particular ligand, whereas it may have high affinity for the ligand in a second oxidation state. Hence, by determining if a metal ion is bound or unbound to a ligand, the oxidation state of the metal ion may be inferred. Such determinations of oxidation state may also be of relevance for monitoring and controlling various processes.

In some embodiments, methods described herein may comprise providing a treatment fluid comprising an ionic material, the ionic material comprising a metal ion; introducing the treatment fluid into a subterranean formation; optically interacting electromagnetic radiation with the ionic material and one or more integrated computational elements, the ionic material being located in a fluid phase comprising the treatment fluid, a formation fluid, or a produced fluid while being optically interacted with the electromagnetic radiation; and determining one or more binding states of the ionic material in the fluid phase, using the one or more integrated computational elements.

As generally discussed above, any type of treatment fluid that may contain a crosslinked polymer at any point during its lifetime may be analyzed according to the present methods in order to determine the binding state of an ionic material. In some embodiments, the treatment fluid may comprise a fracturing fluid. In some or other embodiments, the treatment fluid may comprise a drilling fluid, a completion fluid, or a diversion fluid.

In monitoring a treatment operation, the location at which a fluid phase containing a metal ion is optically interacted with electromagnetic radiation and determination of the binding state is made is also not believed to be particularly limited. Depending on whether one needs to monitor a binding state before, after, or during a treatment operation, or whether one needs to proactively or reactively address the presence of a particular binding state will determine the location(s) at which the analysis of a fluid containing the metal ion may most effectively take place. Illustrative examples of possible analysis scenarios are provided below.

In some embodiments, the treatment fluid can be optically interacted with electromagnetic radiation before it is introduced into the subterranean formation. That is, in some embodiments, optically interacting electromagnetic radiation with the ionic material and one or more integrated computational elements may take place before the treatment fluid is introduced into a subterranean formation. Determining the binding state(s) of the ionic material before its introduction to the subterranean formation may serve as a quality control check of whether the treatment fluid has suitable properties for use in a particular treatment operation. For example, determining the binding state(s) of the ionic material may provide a measure of the extent of crosslinking that has taken place in the treatment fluid and guidance as to whether the treatment fluid is gelled or ungelled. In addition, determining if the ionic material is in the proper binding state can allow one to conclude if the treatment fluid has the capacity for becoming properly gelled. If the treatment fluid is ungelled at the time of measurement, assaying the binding state of the ionic material can determine if the ionic material can eventually initiate crosslinking and gelation of the treatment fluid. For example, if the ionic material is bound by the proper ligands, the ionic material may be released into the treatment fluid in an unbound state at a desired time or location downhole, at which point it may interact with a crosslinkable polymer to initiate crosslinking. However, if the ionic material is bound by the incorrect ligands, the ionic material may be released too slowly in order to initiate effective crosslinking at the proper time downhole. Conversely, if the ionic material enters an unbound state too soon, premature crosslinking may occur, which may be undesirable in some embodiments. In some embodiments, the ionic material can be optically interacted with electromagnetic radiation both before its introduction to a subterranean formation and at some point thereafter.

In some embodiments, methods described herein may comprise formulating a treatment fluid. In more specific embodiments, methods described herein may comprise formulating the treatment fluid with a produced fluid comprising the ionic material. Formulating the treatment fluid with a produced fluid may be particularly advantageous, since it can reduce the need to source and transport an external supply of a carrier fluid for formulating the treatment fluid. Moreover, in some embodiments, an ionic material in a produced fluid may be assayed to determine its binding state therein, as discussed in more detail below. In other embodiments, however, a treatment fluid can be assayed without having first determined the binding states of an ionic material therein. In these and other cases, the composition of the treatment fluid may be adjusted after its formulation to alter one or more of its properties. Specifically, altering one or more properties of the treatment fluid may change one or more binding states of an ionic material that is present therein. Altering one or more properties of the treatment fluid to change one or more binding states of the ionic material may take place such that the treatment fluid has a better capacity for functioning as intended once placed downhole.

In some embodiments, optically interacting electromagnetic radiation with the ionic material and the one or more integrated computational elements may take place while the treatment fluid is located in the subterranean formation. In some embodiments, determining the binding state of the ionic material in the subterranean formation may allow one to determine if the treatment fluid contains a crosslinked polymer and if the treatment fluid is properly gelled in the subterranean formation. For example, determining if the polymer is crosslinked may take place in some embodiments by measuring the distribution of the ionic material between the unbound state and one or more bound states. In some or other embodiments, measuring the distribution between a bound state and an unbound state of an ionic material may allow one to determine if an effective break has occurred and a shut-in period can be ended, for example. In some embodiments, measuring the distribution between a bound state and an unbound state may allow a break time for the treatment fluid to be determined. In some embodiments, if the treatment fluid has not broken or the break has occurred too slowly, the methods described herein may further comprise introducing a breaker to the subterranean formation. Thereafter, the ionic material can again be optically interacted with electromagnetic radiation in order to determine the nature of its binding state(s) in the subterranean formation.

When utilized for analyzing the binding state of an ionic material within a subterranean formation, one or more integrated computational elements may be present in a fixed location within the subterranean formation, or they may be movable. In some embodiments, optical computing devices employing integrated computational element(s) may be affixed at one or more locations within the subterranean formation (e.g., on tubulars). In other embodiments, optical computing devices employing integrated computational element(s) may be removably placed at one or more locations within the subterranean formation, such as through wireline deployment, for example. In related embodiments, optical computing devices employing integrated computational element(s) may be located external to the subterranean formation but be in optical communication therewith by way of an optical fiber or like electromagnetic radiation conduit extending into the subterranean formation. In either case, the integrated computational element(s) may receive electromagnetic radiation from one or more points of interest within the subterranean formation in order to determine the binding state of an ionic material therein.

The methods described herein are not limited to determining if a treatment fluid is gelled or broken based upon the measurement of one or more binding states of an ionic material therein. By extension, one of ordinary skill in the art may utilize such information to determine, for example, if a fluid diversion, chelation, or scaling is occurring in a subterranean formation or Is likely to occur.

Similarly, in some embodiments, optically interacting electromagnetic radiation with the ionic material and the one or more integrated computational elements may take place after producing the ionic material from the subterranean formation. That is, in some embodiments, the ionic material may be optically interacted with electromagnetic radiation while it is in a produced fluid. The produced fluid may be the original treatment fluid, a spent version of the original treatment fluid, another treatment fluid, a breaker fluid, a formation fluid, or any combination thereof. In some embodiments, the produced fluid being analyzed by the methods described herein may comprise a produced aqueous fluid. As alluded to above, in some embodiments, the treatment fluids described herein may be formulated with a produced fluid, particularly a produced aqueous fluid, which can prove advantageous in many instances.

In some embodiments, the methods described herein may further comprise determining if a produced fluid is suitable for reuse in formulating a particular treatment fluid. Such determinations can be problematic using conventional analytical techniques. Depending on the intended function of the ionic material in the treatment fluid after its formulation, the ionic material may be in a bound state or an unbound state in the produced fluid. For example, when it is desired that the ionic material initiate crosslinking of the polymer in the treatment fluid, it may be more desirable for the ionic material in the produced fluid to be in an unbound state. However, if it is desired that the ionic material be present as an inert component of the treatment fluid, or if the ionic material should initiate crosslinking of a polymer in the treatment fluid at a later time, it may be more desirable for the ionic material to be present in a bound state. For example, a treatment fluid may be initially formulated using a produced fluid that contains metal ions bound to a polymer fragment, and the metal ions may be released in an unbound state at later time, if desired. Similarly, it may be more desirable to formulate a treatment fluid using an ionic material in a bound state if a decreased propensity toward scaling is desired. As discussed above, a produced fluid may be further altered in some manner to make it suitable for use in formulating a particular treatment fluid. For example, if an ionic material is present in an unbound state, a suitable complexing species may be added to the produced fluid to form a bound state of the ionic material.

In some embodiments, the treatment fluids being assayed by the methods described herein may further comprise a polymer, particularly a crosslinkable polymer, in addition to the ionic material. In some embodiments, the polymer, a fragment of the polymer, or a monomer related to the polymer may enter into a binding state with the ionic material. In some embodiments, the binding state of the ionic material may result in crosslinking of the polymer, such that the treatment fluid contains a crosslinked polymer. In some or other embodiments, the treatment fluid may initially be gelled and contain a crosslinked polymer. Thereafter, the treatment fluid may be broken by changing the binding state of the ionic material therein. For example, in some embodiments, a crosslinked polymer in a gelled treatment fluid may be formed with a metal ion forming crosslinking bridges between the polymer chains. After breaking occurs, the metal ion may be found in an unbound state, or bound to a fragment of the polymer depending upon whether the crosslinking bridges are directly attacked during the breaking process, or if scission of the polymer molecules occurs instead, with the metal ion remaining bound to the smaller fragments of the original polymer.

In some embodiments, the treatment fluid may comprise a fracturing fluid. In some embodiments, in addition to a polymer and an ionic material, a fracturing fluid may also comprise a plurality of proppant particulates. Proppant particulates are not particularly limited in size or composition and may include, for example, particulates comprising sand, bauxite, ceramic materials, glass materials, polymer materials, polytetrafluoroethylene materials, nut shell pieces, cured resinous particulates comprising nut shell pieces, seed shell pieces, cured resinous particulates comprising seed shell pieces, fruit pit pieces, cured resinous particulates comprising fruit pit pieces, wood, composite particulates, and combinations thereof. Suitable composite particulates may comprise a binder and a filler material wherein suitable filler materials include silica, alumina, fumed carbon, carbon black, graphite, mica, titanium dioxide, meta-silicate, calcium silicate, kaolin, talc, zirconia, boron, fly ash, hollow glass microspheres, solid glass, and combinations thereof. One having ordinary skill in the art will understand suitable ranges for viscosity values of a fracturing fluid in order to transport a plurality of proppant particulates to a desired location within a wellbore. One having ordinary skill in the art will further recognize that a fracturing fluid may be viscosified by a crosslinked polymer.

It is to be recognized that other than the ionic materials described hereinabove, various additional components may be present in the treatment fluids and other compositions described herein. The presence of these additional components is not believed to significantly alter the techniques for assaying the binding state of the ionic material, as described herein. Illustrative components that can be present in any of the treatment fluids described herein include, for example, polymers, acids, acid-generating compounds, bases, base-generating compounds, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, flocculants, scavengers (e.g., $H_2S$ scavengers, $CO_2$ scavengers or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, any combination thereof, and the like.

In some embodiments, methods described herein may comprise: providing a treatment fluid comprising a crosslinkable polymer and an ionic material, the ionic material comprising a metal ion that forms crosslinks between molecules of the crosslinkable polymer; introducing the treatment fluid into a subterranean formation; after introducing the treatment fluid into the subterranean formation, optically interacting electromagnetic radiation with the ionic material and one or more integrated computational elements, the ionic material being located in a fluid phase while being optically interacted with the ionic material; and determining one or more binding states of the ionic material in the fluid phase, using the one or more integrated computational elements, the determining one or more binding states of the ionic material comprising measuring a distribution of the ionic material between an unbound state and one or more bound states, the one or more bound states being selected from the group consisting of a bound state to the polymer, a bound state to a ligand, a bound state to a polymer fragment, a bound state to a monomer, and any combination thereof.

In some embodiments, methods described herein may comprise: optically interacting electromagnetic radiation with an ionic material and one or more integrated computational elements, the ionic material being located in a fluid phase while being optically interacted with the electromagnetic radiation; and determining one or more binding states of the ionic material in the fluid phase, using the one or more integrated computational elements.

In some embodiments, methods described herein may comprise: providing a treatment fluid comprising an Ionic material, the ionic material comprising a metal ion; introducing the treatment fluid into a subterranean formation; optically interacting electromagnetic radiation with the ionic material and one or more integrated computational elements, the ionic material being located in a fluid phase comprising the treatment fluid, a formation fluid, or a produced fluid while being optically interacted with the electromagnetic radiation; and determining one or more binding states of the ionic material in the fluid phase, using the one or more integrated computational elements.

Embodiments disclosed herein include:

A. Methods for determining the binding state of an ionic material. The methods comprise: optically interacting electromagnetic radiation with an ionic material and one or more integrated computational elements, the ionic material being located in a fluid phase while being optically interacted with the electromagnetic radiation; and determining one or more binding states of the ionic material in the fluid phase, using the one or more integrated computational elements.

B. Methods for determining the binding state of an ionic material in a treatment operation. The methods comprise: providing a treatment fluid comprising an ionic material, the ionic material comprising a metal ion; introducing the treatment fluid into a subterranean formation; optically interacting electromagnetic radiation with the ionic material and one or more integrated computational elements, the ionic material being located in a fluid phase comprising the treatment fluid, a formation fluid, or a produced fluid while being optically interacted with the electromagnetic radiation; and determining one or more binding states of the ionic material in the fluid phase, using the one or more integrated computational elements.

C. Methods for determining the binding state of an ionic material in a treatment operation. The methods comprise: providing a treatment fluid comprising a crosslinkable polymer and an ionic material, the ionic material comprising a metal ion that forms crosslinks between molecules of the crosslinkable polymer; introducing the treatment fluid into a subterranean formation; after introducing the treatment fluid into the subterranean formation, optically interacting electromagnetic radiation with the ionic material and one or more integrated computational elements, the ionic material being located in a fluid phase while being optically interacted with the electromagnetic radiation; and determining one or more binding states of the ionic material in the fluid phase, using the one or more integrated computational elements, the determining one or more binding states of the ionic material comprising measuring a distribution of the ionic material between an unbound state and one or more bound states, the one or more bound states being selected from the group consisting of a bound state to the crosslinkable polymer, a bound state to a ligand, a bound state to a polymer fragment, a bound state to a monomer, and any combination thereof.

Each of embodiments A, B, and C may have one or more of the following additional elements in any combination:

Element 1: wherein determining one or more binding states of the ionic material in the fluid phase comprises measuring a distribution of the ionic material between an unbound state and one or more bound states, the one or more bound states being selected from the group consisting of a bound state to a polymer, a bound state to a ligand, a bound state to a polymer fragment, a bound state to a monomer, and any combination thereof.

Element 2: wherein the ionic material comprises a metal ion.

Element 3: wherein the method further comprises determining an oxidation state of the metal ion from the one or more binding states.

Element 4: wherein the method further comprises determining if the fluid phase contains a crosslinked polymer by determining the one or more binding states of the ionic material.

Element 5: wherein the fluid phase comprises a treatment fluid.

Element 6: wherein the method further comprises formulating the treatment fluid with a produced fluid comprising the ionic material.

Element 7: wherein the treatment fluid further comprises a crosslinkable polymer.

Element 8: wherein the method further comprises determining if the crosslinkable polymer is crosslinked by measuring the distribution of the ionic material between the unbound state and the one or more bound states.

Element 9: wherein the treatment fluid is selected from the group consisting of a fracturing fluid, a drilling fluid, a completion fluid, a diversion fluid, and any combination thereof.

Element 10: wherein optically interacting electromagnetic radiation with the ionic material and the one or more integrated computational elements takes place before the treatment fluid is introduced into the subterranean formation.

Element 11: wherein optically interacting electromagnetic radiation with the ionic material and the one or more integrated computational elements takes place while the treatment fluid is located in the subterranean formation.

Element 12: wherein optically interacting electromagnetic radiation with the ionic material and the one or more integrated computational elements takes place after producing the ionic material from the subterranean formation.

Element 13: wherein the method further comprises altering one or more properties of the treatment fluid to change the one or more binding states of the ionic material.

Element 14: wherein the ionic material comprises a metal ion selected from the group consisting of a zirconium ion, an aluminum ion, a titanium ion, a magnesium ion, a calcium ion, and any combination thereof.

Element 15: wherein the method further comprises introducing a breaker into the subterranean formation after determining if the crosslinkable polymer is crosslinked.

Element 16: wherein optically interacting electromagnetic radiation with the ionic material and the one or more integrated computational elements takes place in a produced fluid.

Element 17: wherein the method further comprises detecting the electromagnetic radiation that has optically interacted with the ionic material and the one or more integrated computational elements; and generating an output signal based on the detected electromagnetic radiation, the output signal being correlatable to the one or more binding states of the ionic material in the fluid phase.

By way of non-limiting example, exemplary combinations applicable to A, B, and C include:

The method of A in combination with elements 1 and 2.
The method of A in combination with elements 2 and 3.
The method of A in combination with elements 2 and 5.
The method of A in combination with elements 2, 5 and 7.
The method of A in combination with elements 5, 6 and 7.
The method of A or B in combination with elements 1 and 4.
The method of A or B in combination with elements 1 and 17.
The method of A or B in combination with elements 4 and 10, elements 4 and 11, or elements 4 and 12.
The method of A, B or C in combination with elements 4 and 14.
The method of B or C in combination with elements 8 and 9.
The method of B or C in combination with elements 8 and 14. The method of B or C in combination with elements 9 and 14.
The method of B in combination with elements 1 and 6.
The method of B in combination with elements 7, 8 and 9.
The method of B in combination with elements 7 and 13.
The method of C in combination with elements 8 and 11, or elements 8 and 12.

To facilitate a better understanding of the embodiments of the present disclosure, the following examples of preferred or representative embodiments are given. In no way should the following examples be read to limit, or to define, the scope of the disclosure.

EXAMPLES

Prophetic Example

The optical spectra of a set of fluid samples having a known binding state of an ionic material over a range of concentrations will be prepared. Next, a series of optical transmission interference regression vectors will be generated for the samples, and their performance will be optimized for accuracy, sensitivity and manufacturability by varying the number of layers, the thickness of layers, and/or the material indices of refraction within a design candidate by comparison to the optical spectra. Once one or more suitable design candidates have been identified, an ICE will be manufactured using thin-film or like deposition techniques. The detector output obtained from the ICE will then be calibrated against fluid samples having known concentrations of the binding state to obtain a standard calibration curve. By reading the detector output of an unknown sample, the concentration of a particular binding state will be determined using the calibration curve.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the specification and attached claims are approximations that may vary depending upon the desired properties sought to be obtained in a particular implementation of the present disclosure. At the very least, and not as an attempt to limit the application of the doctrine of equivalents to the scope of the claim, each numerical parameter should at least be construed in light of the number of reported significant digits and by applying ordinary rounding techniques.

What is claimed is the following:

1. A method comprising:
   optically interacting electromagnetic radiation with an ionic material and one or more integrated computational elements, the ionic material being located in a fluid phase while being optically interacted with the electromagnetic radiation; and
   determining one or more binding states of the ionic material in the fluid phase, using the one or more integrated computational elements.

2. The method of claim 1, wherein determining one or more binding states of the ionic material in the fluid phase comprises measuring a distribution of the ionic material between an unbound state and one or more bound states, the one or more bound states being selected from the group consisting of a bound state to a polymer, a bound state to a ligand, a bound state to a polymer fragment, a bound state to a monomer, and any combination thereof.

3. The method of claim 2, wherein the ionic material comprises a metal ion.

4. The method of claim 3, further comprising:
   determining an oxidation state of the metal ion from the one or more binding states.

5. The method of claim 1, further comprising:
   determining if the fluid phase contains a crosslinked polymer by determining the one or more binding states of the ionic material.

6. The method of claim 1, wherein the fluid phase comprises a treatment fluid.

7. The method of claim 1, further comprising:
   detecting the electromagnetic radiation that has optically interacted with the ionic material and the one or more integrated computational elements; and
   generating an output signal based on the detected electromagnetic radiation, the output signal being correlatable to the one or more binding states of the ionic material in the fluid phase.

8. A method comprising:
   providing a treatment fluid comprising an ionic material, the ionic material comprising a metal ion;
   introducing the treatment fluid into a subterranean formation;
   optically interacting electromagnetic radiation with the ionic material and one or more integrated computational elements, the ionic material being located in a fluid phase comprising the treatment fluid, a formation fluid, or a produced fluid while being optically interacted with the electromagnetic radiation; and
   determining one or more binding states of the ionic material in the fluid phase, using the one or more integrated computational elements.

9. The method of claim 8, wherein determining one or more binding states of the ionic material in the fluid phase comprises measuring a distribution of the ionic material between an unbound state and one or more bound states, the one or more bound states being selected from the group consisting of a bound state to a polymer, a bound state to a ligand, a bound state to a polymer fragment, a bound state to a monomer, and any combination thereof.

10. The method of claim 9, further comprising:
    formulating the treatment fluid with a produced fluid comprising the ionic material.

11. The method of claim 9, wherein the treatment fluid further comprises a crosslinkable polymer.

12. The method of claim 11, further comprising:
    determining if the crosslinkable polymer is crosslinked by measuring the distribution of the ionic material between the unbound state and the one or more bound states.

13. The method of claim 11, wherein the treatment fluid is selected from the group consisting of a fracturing fluid, a drilling fluid, a completion fluid, a diversion fluid, and any combination thereof.

14. The method of claim 8, wherein optically interacting electromagnetic radiation with the ionic material and the one or more integrated computational elements takes place before the treatment fluid is introduced into the subterranean formation.

15. The method of claim 14, further comprising:
    altering one or more properties of the treatment fluid to change the one or more binding states of the ionic material.

16. The method of claim 8, wherein optically interacting electromagnetic radiation with the ionic material and the one or more integrated computational elements takes place while the treatment fluid is located in the subterranean formation.

17. The method of claim 8, wherein optically interacting electromagnetic radiation with the ionic material and the one or more integrated computational elements takes place after producing the ionic material from the subterranean formation.

18. The method of claim 8, wherein the ionic material comprises a metal ion selected from the group consisting of a zirconium ion, an aluminum ion, a titanium ion, a magnesium ion, a calcium ion, and any combination thereof.

19. A method comprising:
    providing a treatment fluid comprising a crosslinkable polymer and an ionic material, the ionic material comprising a metal ion that forms crosslinks between molecules of the crosslinkable polymer;
    introducing the treatment fluid into a subterranean formation;
    after introducing the treatment fluid into the subterranean formation, optically interacting electromagnetic radiation with the ionic material and one or more integrated computational elements, the ionic material being located in a fluid phase while being optically interacted with the electromagnetic radiation; and
    determining one or more binding states of the ionic material in the fluid phase, using the one or more integrated computational elements, the determining one or more binding states of the ionic material comprising measuring a distribution of the ionic material between an unbound state and one or more bound states, the one or more bound states being selected from the group consisting of a bound state to the crosslinkable polymer, a bound state to a ligand, a bound state to a polymer fragment, a bound state to a monomer, and any combination thereof.

20. The method of claim 19, wherein optically interacting electromagnetic radiation with the ionic material and the one or more integrated computational elements takes place while the treatment fluid is located in the subterranean formation.

21. The method of claim 20, further comprising:
determining if the crosslinkable polymer is crosslinked by measuring the distribution of the ionic material between the unbound state and the one or more bound states.

22. The method of claim 21, further comprising:
introducing a breaker into the subterranean formation after determining if the crosslinkable polymer is crosslinked.

23. The method of claim 19, wherein optically interacting electromagnetic radiation with the ionic material and the one or more integrated computational elements takes place in a produced fluid.

24. The method of claim 19, wherein the treatment fluid is selected from the group consisting of a fracturing fluid, a drilling fluid, a completion fluid, a diversion fluid, and any combination thereof.

25. The method of claim 19, wherein the ionic material comprises a metal ion selected from the group consisting of a zirconium ion, an aluminum ion, a titanium ion, a magnesium ion, a calcium ion, and any combination thereof.

* * * * *